United States Patent [19]

Mallow et al.

[11] Patent Number: 5,322,797
[45] Date of Patent: * Jun. 21, 1994

[54] METHOD FOR DETECTING VAPOR AND LIQUID REACTANTS

[75] Inventors: William A. Mallow, Helotes; Jerome J. Dziuk, Jr., San Antonio, both of Tex.

[73] Assignee: Southwest Research Institute, San Antonio, Tex.

[*] Notice: The portion of the term of this patent subsequent to Feb. 2, 2010 has been disclaimed.

[21] Appl. No.: 919,788

[22] Filed: Jul. 24, 1992

Related U.S. Application Data

[63] Continuation of Ser. No. 534,198, Jun. 6, 1990, Pat. No. 5,183,763.

[51] Int. Cl.$^5$ .............................................. G01N 33/00
[52] U.S. Cl. .................................... 436/106; 436/3; 436/111; 436/113
[58] Field of Search ........................................ 436/2-3, 436/106, 111, 113; 252/586, 408.1

[56] References Cited

U.S. PATENT DOCUMENTS

| | | | |
|---|---|---|---|
| 3,528,780 | 9/1970 | Radawski | 422/56 |
| 4,201,548 | 5/1980 | Tamaoku et al. | 422/57 |
| 4,223,089 | 9/1980 | Rothe et al. | 435/12 |
| 4,356,149 | 10/1982 | Kitajima et al. | 422/56 |
| 4,420,567 | 12/1983 | McMahon et al. | 436/106 |
| 4,548,906 | 10/1985 | Sekikawa et al. | 436/113 |
| 4,558,043 | 12/1985 | Wenk et al. | 514/210 |
| 4,578,357 | 3/1986 | Melpolder | 436/39 |
| 4,686,171 | 8/1987 | Fifield et al. | 430/273 |
| 4,719,085 | 1/1988 | Jacobs | 422/56 |
| 4,870,049 | 9/1989 | Yamamoto et al. | 427/152 |

OTHER PUBLICATIONS

WPI Acc No. 85-266446/43 JP 60178358 A, Date: Sep. 12, 1985.
WPI Acc No. 89-261687/36 SU 1441219 A, Date: Nov. 30, 1988.

*Primary Examiner*—Lyle A. Alexander
*Attorney, Agent, or Firm*—Richard J. Smith

[57] ABSTRACT

A paint or coating composition and method for detecting vapor or liquid reactants, such as ammonia. The composition is composed of ethyl cellulose as a binder, a filler, such as amorphous silica, and a dye, such as bromophenol blue. The composition serves as a passive detector for vapor or liquid reactants when applied to selected surfaces as a paint. The composition is capable of detecting extremely low concentrations of vapor. Further, the composition is capable of regenerating to its original color, thereby providing repeated detection capability.

3 Claims, No Drawings

METHOD FOR DETECTING VAPOR AND LIQUID REACTANTS

This is a continuation of copending application Ser. No. 07/534,198 filed on Jun. 6, 1990 now U.S. Pat. No. 5,183,763.

FIELD OF THE INVENTION

The present invention relates to a composition and method for detecting vapor and liquid reactants. More particularly, the present invention relates to a composition which may be painted or applied to an object for the purpose of detecting the presence of vapor and liquid reactants, such as ammonia and amino compounds, in proximity to the object. In addition, the present invention relates to the significantly enhanced sensitivity derived by the presence of amorphous silica in the composition.

BACKGROUND

The detection of the presence of certain vapors or liquid reactants, such as ammonia or amino compounds, is quite important, particularly when the presence of such vapors or liquid reactants indicates the presence of toxic chemicals or biological warfare agents, or the undesirable leakage of a gas from an enclosure. A number of prior apparatus and methods for detecting vapors and liquid reactants are known in the art. Nevertheless, the art does not teach or suggest a sprayable, brushable, or trowelable paint which incorporates in its dried film the combined properties of vapor permeable, liquid repellant film and an accessible indicator which can detect extremely low concentrations of reactant, such as ammonia, and regenerate the original color. More particularly, prior art does not teach the extraordinary contribution of amorphous silica as intensifier of sensitivity.

SUMMARY OF THE INVENTION

Accordingly, the present invention provides a composition and method for detecting the presence of vapor or liquid reactants or reagents, such as ammonia or amino compounds. The composition or formulation of the present invention includes a binder, filler, and dye in a single mixture which can be applied to selected surfaces as a paint. The composition serves as a passive detector for detecting extremely low concentrations of vapor or liquid reactants, such as ammonia. Further, the composition is capable of regenerating to its original color, thereby providing repeated detection capability.

The composition of the present invention is composed of a binder, a filler, and a dye. The binder is preferably ethyl cellulose, the filler is preferably amorphous silica, which also serves as intensifier of sensitivity, and the dye is preferably an indicator such as bromophenol blue. The composition is further composed of a solvent, such as a blend of butyl acetate, toluene and acetone, for dissolving the binder. A plasticizer, such as glycerol, may be included in the composition. An acid or base, such as nitric acid, may also be added to the composition for adjusting the pH to a desired level.

The composition or mixture of the present invention is made by dissolving the binder in the solvent and stirring in the dye, glycerol, and amorphous silica. If bromophenol blue is the dye, the mixture is then titrated with nitric acid to give a stable yellow color from the original yellow-green created by the bromophenol blue.

The composition of the present invention may be utilized for detecting chemical or biological warfare agents and for monitoring respiratory gases. In either application, the composition of the present invention is applied to an object and the color change of the composition is thereafter sensed, either visually or with appropriate instrumentation. The degree of color change may also be measured. The composition of the present invention may also be utilized for detecting leakage from an enclosure by introducing a predetermined gas to the enclosure, applying the composition of the present invention to the exterior of the enclosure or an object adjacent to the exterior of such enclosure, and sensing the color change in the composition, either visually or with appropriate instrumentation. The degree of color change of the composition may also be measured.

The present invention therefore provides a sprayable, brushable, or trowelable paint which incorporates in its dried film the combined properties of vapor permeable, liquid repellant film and an accessible indicator which can detect extremely low concentrations of a reactant, owing to the presence of amorphous silica, and regenerate to the original color.

DETAILED DESCRIPTION OF THE PREFERRED EMBODIMENT

The composition of the present invention is composed of a binder, a filler, and a dye. The binder is preferably ethyl cellulose, the filler is preferably amorphous silica, and the dye is preferably an indicator or dye such as bromophenol blue. The composition is further composed of a solvent, such as a blend of butyl acetate, toluene and acetone, for dissolving the binder. A plasticizer, such as glycerol, may be included in the composition. Nitric acid may also be added to the composition for adjusting the pH to a desired level. The basic ingredients and approximate percentages by weight are illustrated in Chart A hereinbelow:

| CHART A | |
| --- | --- |
| Ingredients | Percentage by Weight |
| Ethyl Cellulose | 10% |
| Amorphous Silica | 10% |
| Solvent | 79.8% |
| Indicator | 0.2% |

The ingredients and ranges of each ingredient in parts by weight for the composition of the present invention for detecting amines and nitrogen type compounds, such as ammonia ($NH_3$), are illustrated in Chart B hereinbelow:

| CHART B | |
| --- | --- |
| Ingredients | Range (Parts by Weight) |
| Ethyl Cellulose | 6–24 |
| Butyl Acetate | 20–65 |
| Toluene | 20–65 |
| Acetone | 5–45 |
| Bromophenol Blue | 0.1–0.5 |
| Glycerol | 0–5 |
| Amorphous Silica | 4–25 |
| Nitric Acid | 0–0.5 |

The following examples are presented to illustrate the composition of the present invention in a more detailed manner.

EXAMPLE 1

| Ingredients | Parts by Weight | Percentage by Weight |
| --- | --- | --- |
| Ethyl Cellulose | 12 | 9.67% |
| Butyl Acetate | 50 | 40.0% |
| Toluene | 50 | 40.0% |
| Acetone | 5 | 4.0% |
| Glycerol | 3 | 3.0% |
| Bromophenol Blue | 0.2 | 0.2% |
| Amorphous Silica | 4 | 3.0% |
| Nitric Acid | 2 drops | .13% |

EXAMPLE 2

| Ingredients | Parts by Weight | Percentage by Weight |
| --- | --- | --- |
| Ethyl Cellulose | 12 | 9.14% |
| Butyl Acetate | 50 | 40.0% |
| Toluene | 50 | 40.0% |
| Acetone | 5 | 4.0% |
| Glycerol | 3 | 2.0% |
| Bromophenol Blue | 0.2 | 0.2% |
| Amorphous Silica | 6 | 4.5% |
| Nitric Acid | 2 drops | .16% |

EXAMPLE 3

| Ingredients | Parts by Weight | Percentage by Weight |
| --- | --- | --- |
| Ethyl Cellulose | 12 | 9.42% |
| Butyl Acetate | 50 | 39.0% |
| Toluene | 50 | 39.0% |
| Acetone | 5 | 4.0% |
| Glycerol | 3 | 2.3% |
| Bromophenol Blue | 0.2 | 0.2% |
| Amorphous Silica | 8 | 6.0% |
| Nitric Acid | 1 drop | .08% |

EXAMPLE 4

| Ingredients | Parts by Weight | Percentage by Weight |
| --- | --- | --- |
| Ethyl Cellulose | 12 | 9.4% |
| Butyl Acetate | 50 | 37.0% |
| Toluene | 50 | 37.0% |
| Acetone | 5 | 3.7% |
| Glycerol | 3 | 2.2% |
| Bromophenol Blue | 0.2 | 0.2% |
| Amorphous Silica | 14 | 10.5% |
| Nitric Acid | 0 drops | 0% |

EXAMPLE 5

| Ingredients | Parts by Weight | Percentage by Weight |
| --- | --- | --- |
| Ethyl Cellulose | 12 | 8.48% |
| Butyl Acetate | 50 | 36.7% |
| Toluene | 50 | 36.7% |
| Acetone | 5 | 3.6% |
| Glycerol | 3 | 2.0% |
| Bromophenol Blue | 0.2 | 0.2% |
| Amorphous Silica | 16 | 12.0% |
| Nitric Acid | 4 drops | .32% |

The foregoing examples are intended to be purely exemplary of the present invention. For example, although glycerol has been found to do the job of plasticizing without severe loss of sensitivity, alternate plasticizers for ethyl cellulose may be utilized in place of glycerol, such as ethylene glycol, propylene glycol or castor oil. Further, MEK (methylethylketone) may be utilized in place of acetone and xylene may be utilized in place of toluene. Although butyl acetate provides rapid drying and good solvency, ethyl acetate or amyl acetate may be utilized in place of butyl acetate. Finally, the amorphous silica utilized in the present invention may be silicic acid, diatomaceous silica, pyrogenic silica, biogenic silica or silica gel.

It is to be understood that, although bromophenol blue may be utilized as the dye for amines and nitrogen type compounds, such as ammonia ($NH_3$), alternate indicators may be utilized in place of bromophenol blue to provide a reagent specific indicator. For example, methylene red may be utilized as the dye for detecting changes in pH in the atmosphere irrespective of ammonia. Lead acetate may be utilized as the dye for detecting hydrogen sulfide in the atmosphere. Silver nitrate may be utilized as the dye to detect halogens, such as chlorine or fluorine. Bromocresol green and bromothymol blue may also be utilized as indicators for certain reagents. That is, the particular indicator may be selected for the acid or alkali which it is desired to detect such that the composition of the present invention may be utilized to detect almost any atmospheric reagent or contaminant by varying the indicator. The pH adjusting acid or alkali material, such as nitric acid, may also be varied depending upon the indicator selected. For example, acetic acid may be used as a pH adjustor for methylene red.

The composition or mixture of the present invention is made by dissolving the binder in the solvent and stirring in the dye and amorphous silica. A plasticizer, such as glycerol, may also be stirred into the mixture. The mixture may then be titrated with an appropriate pH adjustor. If bromophenol blue is the indicator, as exemplified hereinabove, the mixture is then titrated with nitric acid to give a stable yellow color from the original yellow-green created by the bromophenol blue. The resultant mixture is a homogeneous liquid slurry which is water insoluble and which may be sprayed or brushed on a selected surface as a paint.

The composition of the present invention may be used by applying the composition to a selected surface as a paint and allowing the composition to dry on the surface. When the dried composition is exposed to a vapor or liquid reactant such as ammonia, the coating undergoes a distinctive and immediate color change. For example, the color will change from yellow to deep blue when utilizing a composition exemplified by the foregoing examples to detect ammonia. Further, the degree of color change increases with the degree or extent of ammonia exposure. However, the coating composition of the present invention provides a reversible phenomenon such that the composition reverses back to its original color (e.g., yellow) after a period of time. As such, the coating composition of the present invention may be utilized to detect the particular vapor or liquid reagent on repeated occasions.

It has been found that ethyl cellulose provides a desired combination of a water insoluble binder and a highly permeable membrane to let the detected gases, such as ammonia vapor, through. That is, ethyl cellulose provides a desired vehicle for transfer of vapor to the indicator and a binder for attaching the indicator to a wide variety of substrate materials, such as minerals, metals and papers.

While not wishing to be bound by theory, it is believed that the increased reagent sensitivity provided by the composition of the present invention is obtained as a result of the presence of amorphous silica, which orients the dye and enhances the dye's response to reagents. That is, it is believed that the amorphous silica absorbs the dye on its surface and helps to orient it in the composition film so that a higher number of dye molecules are available per unit of area or volume for response to the reagent. The amorphous silica therefore serves as a pigment, filler, substrate for dye, and sensitizer in the composition of the present invention.

It is to be understood that the sensitivity of the composition of the present invention can be varied depending upon the sensitivity desired for a particular application. As illustrated in Examples 1-5 hereinabove, sensitivity can be varied by varying the amount of amorphous silica in the composition. That is, ammonia sensitivity increases from Example 1 to Example 5 such that Example 2 is more sensitive than Example 1, Example 3 is more sensitive than Example 2, Example 4 is more sensitive than Example 3, and Example 5 is more sensitive than Example 4. Further, the sensitivity of various composition examples can be compared by degrees of color change. Finally, the degree of color change increases with increasing levels of reagent exposure. The degree of color change of the composition of the present invention can be measured by a color range chart similar to that used for measuring color change of litmus paper or by photospectroscopy instrumentation.

The composition of the present invention may be utilized for detecting extremely low concentrations of gases, such as ammonia. For example, tests on the composition identified as Example 5 hereinabove have indicated a sensitivity to ammonia in the range of 1 part per $10^{20}$ to all higher concentrations. In one test a quantity of gaseous ammonia was diluted to 1 part in $10^{20}$ parts. This was done by filling a 10 ml volumetric syringe with ammonia and exhausting all except 1 ml, refilling with air to the 10 ml level and exhausting again, repeating this one hundred times, thereby assuring a fresh supply of uncontaminated air with each cycle. Even after such exhaustive dilution, a piece of paper painted with the composition of Example 5 hereinabove delivered a bright blue response to the residue of air in the syringe.

In another test a measured volume of ammonia gas (i.e., 1 ml) was injected into a 10 liter vessel which was then cyclically exhausted to reduce the concentration to 5 to 1 part per billion and less. A photoelectric cell was then used to monitor a laser reflectance/absorbance signal as the gas was discharged onto a piece of paper, painted with the composition of Example 5 hereinabove, as it travelled past the light monitoring cell. The photoelectric cell measured the color change of the paper, the intensity of which was registered on a millivolt meter. This later test was conducted with a variety of concentrations of ammonia gas prepared by dilution in fixed volume vessels.

The composition of the present invention has numerous applications including, but not limited to, the detection of chemical and biological warfare agents, such as those which contain polypeptides or amino acids. For example, the composition of the present invention may be applied to a soldier's clothing whereupon the color of the composition on the clothing will change upon exposure to the undesirable chemical vapor. The color change can be sensed visually or by alternate means and the degree of color change may be measured. The composition of the present invention may also be utilized in surgical applications, such as to monitor respiratory gases. For example, the composition of the present invention may be applied to a strip of material which is placed in proximity to the expelled respiratory gases of a patient. By sensing the color change of the composition on the material it is possible to thereby monitor particular vapors, such as carbon dioxide, in the respiratory gases. Once again, the sensing of color change can be done visually or by instrumentation and the degree of color change can be measured.

The composition of the present invention may be used for detecting leakage from an ammonia based refrigerant system. The composition, such as Example 5 hereinabove, is applied to the exterior of the system adjacent to a suspected refrigerant leak. The color change of the composition is thereafter sensed, either visually or with appropriate instrumentation. A change in color of the composition from yellow to blue indicates leakage of refrigerant from the system. The degree of color change may also be measured to thereby provide an indicator of the severity of the leak.

The composition of the present invention may also be used for detecting leakage of vapor, such as ammonia, from an enclosure, such as an airplane fuselage. In this method of use, a predetermined amount of detectable gas is introduced into the enclosure and the composition of the present invention is applied to the exterior of the enclosure or an object adjacent to the enclosure. The color change of the composition is thereafter sensed such that upon change of color, the presence of the selected gas exterior to the enclosure is thereby detected. The sensing of the color change of the composition may be done visually or with instrumentation and the degree of color change can be measured.

It is to be understood that the amorphous silica utilized in the present invention may be the amorphous silica sold under the trademark Syloid 244 by W. R. Grace Co., which material is a finely divided amorphous silica of −244 mesh. The ethyl cellulose utilized in the present invention may be the grade N-7 by Hercules, which material has a molecular weight distribution that facilitates good binding while not inhibiting gas passage through the composition film and allowing a good exchange of gas. The N-7 grade represents an intermediate level of ethoxy group substitution of the celluloric skeleton and a low molecular weight distribution, as well as a low viscosity solution.

While the composition and method for detecting vapor and liquid reactants has been described in connection with the preferred embodiment, it is not intended to limit the invention to the particular form set forth, but on the contrary, it is intended to cover such alternatives, modifications, and equivalents as may be included within the spirit and scope of the invention as defined by the appended claims.

What is claimed is:

1. A method for detecting leakage from an enclosure, comprising the steps of:
   (a) introducing a predetermined gas to said enclosure, said gas comprising nitrogen containing compounds of the class comprising amines and ammonia;
   (b) providing a composition capable of a detectable colorimetric change to an object adjacent to said enclosure, said composition consisting essentially of ethyl cellulose, at least 3.0% by weight amorphous silica, solvent and an indicator; and (c) sensing any color change of said composition which indicates the presence of said predetermined gas and leakage from said enclosure.

2. A method for detecting leakage from an enclosure, as recited in claim 1, further comprising the step of measuring the degree of color change of said composition.

3. A method for detecting leakage from an enclosure, comprising the steps of:
   (a) introducing a predetermined gas to said enclosure, said gas comprising nitrogen containing compounds of the class comprising amines and ammonia;
   (b) providing a composition capable of a detectable colorimetric change to an object adjacent to said enclosure, said composition consisting essentially of ethyl cellulose, at least 3.0% by weight amorphous silica, solvent and an indicator; and
   (c) measuring the degree of color change of said composition which indicates the presence of said predetermined gas and leakage from said enclosure.

* * * * *